United States Patent [19]

Kwong

[11] Patent Number: 5,792,066

[45] Date of Patent: Aug. 11, 1998

[54] METHOD AND SYSTEM FOR DETECTING ACUTE MYOCARDIAL INFARCTION

[75] Inventor: Manlik Kwong, Corvallis, Oreg.

[73] Assignee: Hewlett-Packard Company, Palo Alto, Calif.

[21] Appl. No.: 780,648

[22] Filed: Jan. 9, 1997

[51] Int. Cl.$^6$ .................................................. A61B 5/0452
[52] U.S. Cl. ................................................................. 600/517
[58] Field of Search ................................. 128/696, 702, 128/704; 600/509, 515, 517

[56] References Cited

U.S. PATENT DOCUMENTS

| | | | |
|---|---|---|---|
| 4,546,776 | 10/1985 | Bellin et al. | 128/704 |
| 4,957,115 | 9/1990 | Selker | 128/696 |
| 5,277,188 | 1/1994 | Selker | 128/696 |

*Primary Examiner*—William E. Kamm
*Assistant Examiner*—George R. Evanisho

[57] ABSTRACT

A method and system for determining Acute Myocardial Infarction. The method and system work by determining whether or not at least one pre-specified component wave is present within each successive heartbeat waveform (e.g. the S wave component of the QRSTU waveform) appearing within each electrocardiographic lead. After it has been determined whether or not the pre-specified component wave is present within the heartbeat waveforms under consideration (each lead will generally have some representation of each successive heartbeat waveform present within it), a wave amplitude ratio (e.g. the ST complex amplitude divided by the S wave component amplitude at some specified instant in time) is calculated. Thus, for each successive heartbeat waveform there will generally be at least one wave amplitude ratio calculated for each electrocardiographic lead, since the same heartbeat waveform generally appears, in some form, within each electrocardiographic lead. Finally, the calculated wave amplitude ratios, which are generally calculated on each lead that every successive heartbeat waveform, are compared to predetermined criteria (e.g. traversing a classification tree), and on the basis of this comparison it is indicated whether Acute Myocardial Infarction is occurring.

8 Claims, 5 Drawing Sheets

METHOD AND SYSTEM FOR DETECTING ACUTE MYOCARDIAL INFARCTION

BACKGROUND

1. Technical Field

The present invention relates, in general, to an improved method and system to be utilized in monitoring electrocardiographic waveform data and, in particular, to an improved method and system to be utilized in monitoring electrocardiographic waveform data and which can detect the presence of Acute Myocardial Infarction, even in patients who have underlying heart conditions which mimic Acute Myocardial Infarction. Still more particularly, the present invention relates to an improved method and system to be utilized in monitoring electrocardiographic waveform data and which can detect the presence of Acute Myocardial Infarction, even in patients who have underlying heart conditions which mimic Acute Myocardial Infarction, by creating patient-specific data sets and making the assessment of the existence of an Acute Myocardial Infarction on the basis of both the created patient-specific data sets and statistical criteria.

2. Description of Related Art

The present invention remedies a deficiency in the prior art methods and systems for detecting Acute Myocardial Infarction (AMI) on the basis of a patient's electrocardiographic waveform data. The deficiency remedied is that the prior art methods and systems are unable to detect AMI on the basis of a patient's electrocardiographic waveform data when such patient has an underlying heart condition which mimics standard AMI electrocardiographic detection criteria. In the methods and systems existing within the prior art, no attempt is made to detect AMI in such patients. Rather, in the prior art the patient's electrocardiographic data is prescreened for the presence of underlying heart conditions which mimic standard AMI detection criteria, and if such conditions are found the prior art methods and systems simply refuse to attempt AMI detection for such patients.

Both the prior art and the present invention utilize certain specific electrical signals (known as "leads") derived from a device for monitoring heart function known as the electrocardiograph. In order to understand how these certain specific electrical signals are utilized, it is helpful to have a basic understanding of the electrocardiograph and to what the certain specific electrical signals refer. Accordingly, as an aid to understanding the electrocardiograph, the discussion below presents a brief description of (1) the electrochemical and mechanical operation of the heart, (2) how the electrochemical operation of the heart is transduced into electrical energy which is then used by the electrocardiograph to graphically denote the mechanical operation of the heart, and (3) how the certain specific electrical signals (or "leads") are derived from the electrocardiograph.

The mechanical events of the heart are preceded and initiated by the electrochemical activity of the heart (i.e., the propagation of the action potential). There is a device which transforms the electrochemical activity of the heart into a form visible to the human eye: the electrocardiograph, which produces a visual representation of the electrochemical activity of the heart. The visual representation is known as the electrocardiogram (EKG).

During an EKG, electrodes are attached to the body surface. The electrodes are specially treated to allow the charge carriers within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG MONITOR is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, a normal heartbeat has a distinctive signal. Initially, the galvanometer notes a relatively short duration rounded positive deflection (known as the P wave), which is believed to be caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When these waves are taken together, they are known as the QRS complex. The QRS complex is believed to be caused by ventricular depolarization. Subsequent to the QRS complex is a relatively long duration rounded positive deflection (known as the T wave), which is believed to be caused by ventricular repolarization.

The EKG, in practice, uses many sets of electrodes. But these electrodes are so arranged on the surface of the body such that the signal received will have the similar shape as that just described. Well-known bipolar pairs of electrodes are typically located on a patient's right arm (RA), left arm (LA), right leg (RL) (commonly used as a reference), and left leg (LL). Monopolar electrodes referenced properly are referred to as V leads and are positioned anatomically on a patient's chest according to an established convention. In heart monitoring and diagnosis, the voltage differential appearing between two such electrodes or between one electrode and the average of a group of other electrodes represents a particular perspective of the heart's electrical activity and is generally referred to as the EKG. Particular combinations of electrodes are called leads. For example, the leads which may be employed in a standard twelve-lead electrocardiogram system are:

Lead I=(LA−RA)
Lead II=(LL−RA)
Lead III=(LL−LA)
Lead V1=V1−(LA+RA+LL)/3
Lead V2=V2−(LA+RA+LL)/3
Lead V3=V3−(LA+RA+LL)/3
Lead V4=V4−(LA+RA+LL)/3
Lead V5=V5−(LA+RA+LL)/3
Lead V6=V6−(LA+RA+LL)/3
Lead aVF=LL−(LA+RA)/2
Lead aVR=RA−(LA+LL)/2
Lead aVL=LA−(RA+LL)/2

Thus, although the term "lead" would appear to indicate a physical wire, in electrocardiography the term actually means the electrical signal taken from a certain electrode arrangement as illustrated above.

Over the years, health care professionals have built up a body of knowledge wherein they have learned to coordinate variations in and data from the EKG with different diseases and heart defects. Formally, this process of coordinating is known as "electrocardiography."

Within electrocardiography, EKG data serves many purposes. One of the purposes served is determining when and whether a patient's heart has entered AMI. Myocardial Infarction, or a heart attack, is the term used to describe the death of a portion of the heart muscle and generally is caused by an insufficient blood supply to the heart due to an occlusion of the coronary arteries. Acute means it is in the process of happening.

A heart attack will occur when a coronary artery is permanently occluded, or blocked for longer than about 30 minutes. When a blockage occurs for such a length of time, the myocardium, the region of the cardiac muscle supplied by the coronary artery, is starved for oxygen and nutrients for so long that permanent damage (necrosis) occurs. The entire body, which depends on the blood supply supported by the pumping action of the heart, is affected by a heart attack. During a severe attack the heart may pump just enough blood to keep the body alive. The lungs fill with fluid and the kidneys cannot clear the blood stream of waste. The victim may be confused because the brain is not receiving enough oxygen. These are also symptoms of shock. A Myocardial Infarction generally causes anginal pain for longer than 15 minutes, but it is also possible to have a "silent" heart attack in which no symptoms appear. The evidence of a silent heart attack may show up on an electrocardiogram or other tests on the heart.

The general criteria for determining whether a patient is suffering AMI on the basis of EKG data is to look for elevation in the ST segment in various leads. For example, when an Inferior Myocardial Infarction occurs, generally there is ST segment elevation in leads II, III, and aVF, and ST segment elevation in these leads is used as the major criteria for detection of AMI; when either an Anterior or Anterolateral Myocardial Infarction occurs generally there is an ST segment elevation in leads V2–V5, and ST segment elevation in these leads is used as the major criteria for detection of AMI.

The use of such criteria works well for the majority of patients, and most automated systems designed to detect AMI use some or all of these criteria to detect the presence of AMI. However, there is a sub-population of patients who have heart conditions such that their "normal" (for those patients), or usual, EKG will show elevated ST segments in the very same leads which are generally used to detect AMI.

Obviously, one can't use the standard criteria for determining whether a patient within the sub-population has AMI since the patient's "normal" (that is, the usual state of affairs for that patient) EKG will be similar to the standard criteria for detecting AMI, and thus such a patient's "normal" EKG could register as a "false positive" in that it would be detected as an AMI when in reality such was not occurring. Thus, a need exists for a method and system for detecting AMI in the sub-population of patients who have "normal" (that is, the usual state of affairs for those patients) EKG patterns which mimic standard AMI detection criteria.

This need has not been addressed within the prior art. In the prior art, these patients are merely excluded from consideration. That is, in the prior art the patient's EKG data is prescreened for an indication that the patient has an underlying condition which mimics standard AMI detection criteria. This prescreening is done by screening for other waveform characteristics which are associated with the underlying conditions, but which are not associated with "normal" patient's with AMI. Those skilled in the art will recognize that such characteristics are legion, but one example of such is the prescreening criteria that detects Left Ventricular Hypertrophy by looking for standard AMI detection criteria occurring relatively contemporaneously with one of the following: (1) the S wave amplitude in lead V1 and the R wave amplitude in lead V5 summing to 3.5 mV or more; (2) R wave amplitude greater than 2.5 mV in lead V1–V5; or (3) S wave amplitude greater than 2.5 mV in leads V1–V2. Another example is the prescreening criteria that detects Right Bundle Branch Block by looking for standard AMI detection criteria occurring relatively contemporaneous with one of the following: (1) QRS duration greater than or equal to 135 milliseconds in one or more of leads V1, V2, or V3 and R wave duration less than or equal to 39 milliseconds in lead V1; or (2) QRS duration greater than or equal to 140 milliseconds or more in any two of leads V1, V2, or V3. If such an underlying condition is detected, the patient data is shunted off and not subjected to any AMI detection criteria. Thus, while the prior art alleviates the risk of getting a false positive AMI detection for such patients, it makes no attempt to detect the presence of AMI in such patients.

Thus it is apparent that a need exists for the present invention: a system and method which can detect AMI in patients whose underlying conditions mimic standard AMI detection criteria.

SUMMARY OF THE INVENTION

It is therefore one object of the present invention to provide an improved method and system to be utilized in monitoring EKG waveform data.

It is another object of the present invention to provide an improved method and system to be utilized in monitoring EKG waveform data and which can detect the presence of AMI, even in patients who have underlying heart conditions which mimic Acute Myocardial Infarction.

It is yet another object of the present invention to provide an improved method and system to be utilized in monitoring EKG waveform data and which can detect the presence of Acute Myocardial Infarction, even in patients who have underlying heart conditions which mimic Acute Myocardial Infarction, by creating patient-specific data sets and making the assessment of the existence of an Acute Myocardial Infarction on the basis of both the created patient-specific data sets and statistical criteria.

The foregoing objects are achieved as is now described. The method and system work by determining whether or not at least one pre-specified component wave is present within each successive heartbeat waveform (e.g. the S wave component of the QRSTU waveform) appearing within each electrocardiographic lead. After it has been determined whether or not the pre-specified component wave is present within the heartbeat waveforms under consideration (each lead will generally have some representation of each successive heartbeat waveform present within it), a wave amplitude ratio (e.g. the ST complex amplitude divided by the S wave component amplitude at some specified instant in time) is calculated. Thus, for each successive heartbeat waveform there will generally be at least one wave amplitude ratio calculated for each electrocardiographic lead, since the same heartbeat waveform generally appears, in some form, within each electro-cardiographic lead. Finally, the calculated wave amplitude ratios, which are generally recalculated for each lead on every successive heartbeat waveform, are compared to predetermined criteria (e.g. traversing a classification tree), and on the basis of this comparison it is indicated whether Acute Myocardial Infarction is occurring.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
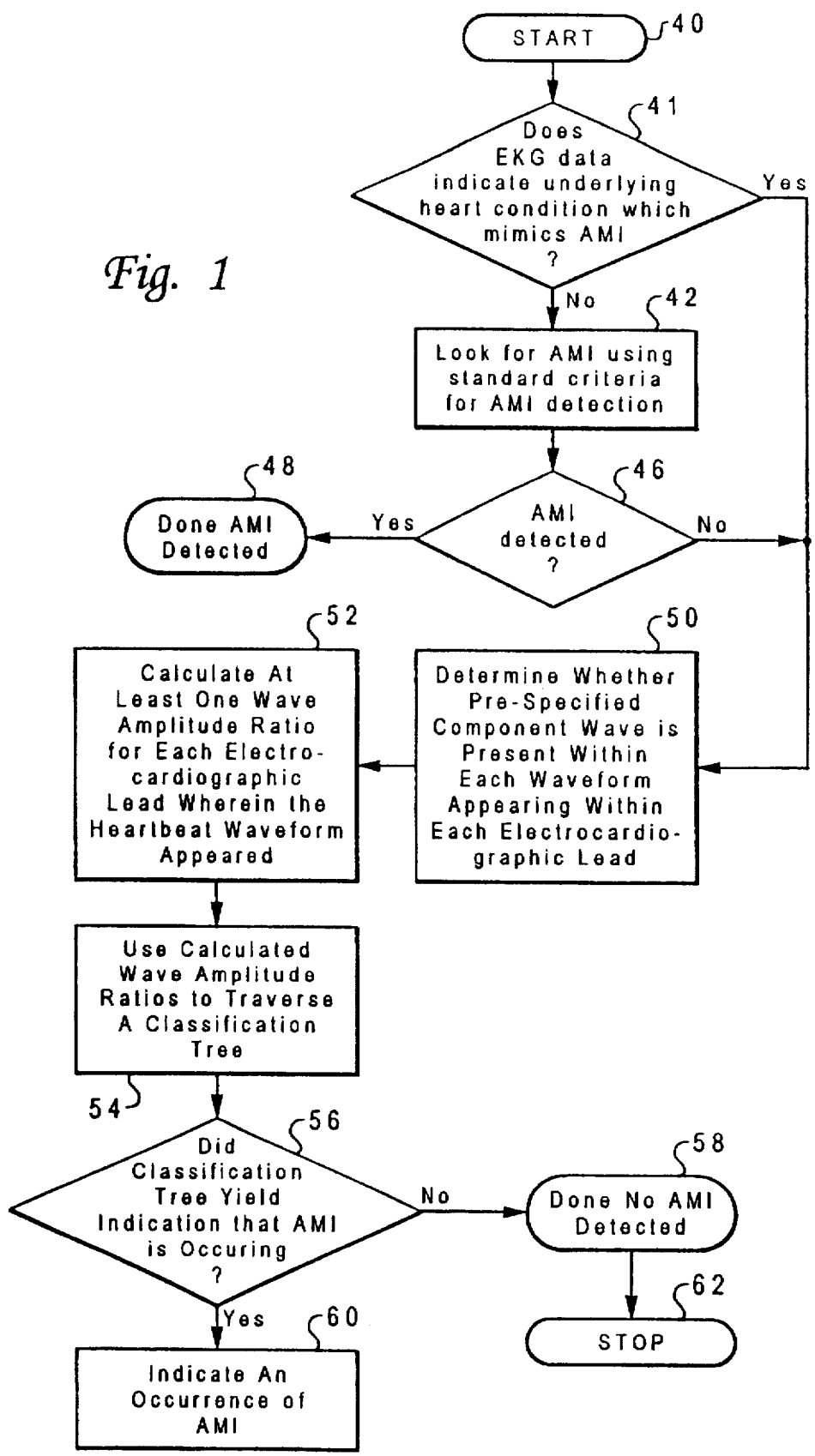
FIG. 1 is a high-level logic flowchart depicting the method and process whereby the present invention detects the occurrence of Acute Myocardial Infarction.

With reference now to the figures and in particular with reference now to FIG. 1, it can be seen that FIG. 1 is a high level logic flowchart depicting the method and process whereby the present invention detects the occurrence of AMI. The flowchart depicts the steps necessary for one specific waveform of a patient's EKG waveform data. Thus, the steps shown will generally be performed for every successive heartbeat waveform within the patient's EKG data.

Method step 40 illustrates the start of the process. Method step 41 shows a prescreening decision point, wherein it is determined whether certain criteria within the EKG waveform under examination indicate that the patient has an underlying condition which mimics standard AMI detection criteria. Those skilled in the art will recognize that such criteria are legion, but one example of such is the prescreening criteria that detects Left Ventricular Hypertrophy by looking for standard AMI detection criteria occurring relatively contemporaneously with one of the following: (1) the S wave amplitude in lead V1 and the R wave amplitude in lead V5 summing to 3.5 mV or more; (2) R wave amplitude greater than 2.5 mV in lead V1-V5; or (3) S wave amplitude greater than 2.5 mV in leads V1-V2. Another example is the prescreening criteria that detects Right Bundle Branch Block by looking for standard AMI detection criteria occurring relatively contemporaneously with one of the following: (1) QRS duration greater than or equal to 135 milliseconds in one or more of leads V1, V2, or V3 and R wave duration less than or equal to 39 milliseconds in lead V1; or (2) QRS duration greater than or equal to 140 milliseconds or more in any two of leads V1, V2, or V3. If such an underlying condition is not detected, the waveform is fed through to Method step 42. Method step 42 illustrates the way in which the prior art detected AMI. Those skilled in the art will be appreciate that there are a multitude of ways that this was done in the prior art. For example, ST segment elevation in leads V2 through V5, as was discussed above.

Method step 46 depicts a decision point. If method step 42 indicated that an AMI was detected, then at this decision point one would immediately go to method step 48, note that the AMI had been detected, and stop. If method step 42 did not detect the presence of a AMI, then one would immediately flow through to method step 50. The reason that the data will still be delivered to method step 50, even though the prescreening of method step 41 did not detect an underlying condition which mimics standard AMI detection criteria, is that the EKG waveform could have been a very weak signal with borderline ST segment elevation and thus could still be indicative of AMI. That is, failure of the prescreening criteria of Method step 50 does not necessarily mean that no AMI is present.

Method step 50 shows the determination of whether or not at least one pre-specified component wave is present within the heartbeat waveform appearing within each electrocardiographic lead (in the preferred embodiment, the component wave is the S wave). That is, with it understood that a version of this electrocardiographic heartbeat waveform will generally appear within each of the electrocardiographic leads, a determination is made as to whether a pre-specified component wave is present within the different versions of the same heartbeat waveform appearing within each of the electrocardiographic leads.

Method step 52 depicts the calculation of at least one wave amplitude ratio for each electrocardiographic lead wherein the heartbeat waveform appeared. That is, with it understood that a version of that electrocardiographic heartbeat waveform will generally appear within each of the electrocardiographic leads, it is, to be understood that at least one waveform amplitude ratio will generally be calculated for each electrocardiographic lead wherein a version of the heartbeat waveform appeared. In the preferred embodiment, the ST/S wave amplitude ratio is calculated by dividing the ST amplitude at J-point, midpoint, and J-point plus 80 milliseconds by the maximum amplitude of the S-wave. All of which yield satisfactory results.

In the preferred embodiment, the ST/S wave amplitude ratio is not currently being calculated for every successive waveform received, although it clearly can be, but rather is calculated on 10 or 11 seconds of electrocardiographic data. There are two variations of this technique currently used in the preferred embodiment: either (1) a specific single waveform is extracted from the 10 or 11 seconds of electrocardiographic data in order to calculate the ST/S wave amplitude ratio; or (2) a mean ST segment amplitude is calculated from all ST segments contained within the 10 or 11 seconds of data, and a mean S wave amplitude is calculated from all S waves contained within the 10 or 11 seconds of data, and these resulting averages are subsequently used to calculate the ST/S wave ratio.

Method step 54 illustrates the comparison of each calculated wave amplitude ratio obtained within method step 52 to certain predetermined criteria. Specifically, method step 54 shows that the calculated wave amplitude ratios are used to traverse a classification tree. This classification tree is set forth in FIG. 3 and will be discussed below. If the classification tree yields the indication that the electrocardiographic heartbeat waveforms appearing within each electrocardiographic lead indicated that an AMI is occurring, then one proceeds to method step 60 wherein the occurrence of an AMI is indicated. Otherwise, if the classification tree did not yield an indication that AMI is occurring, one proceeds to method step 58 which depicts the result that no AMI was detected. Method step 62 illustrates the end of the process for the heartbeat waveform under scrutiny. Upon the next received successive waveform the process will restart with method step 40.

Figure 2:
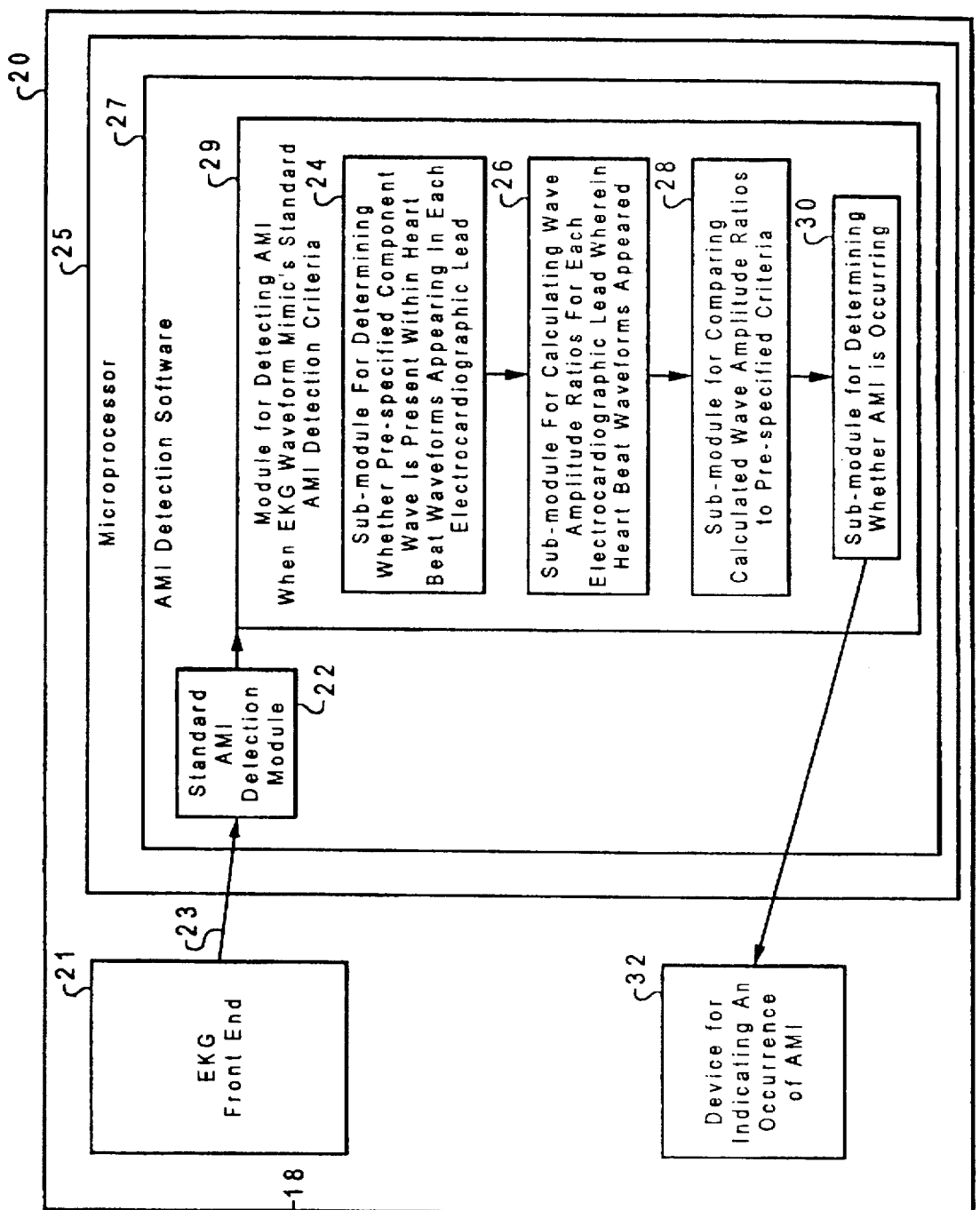
FIG. 2 illustrates a high-level schematic view of a system for implementing the present invention.

Referring now to FIG. 2, there is depicted a high level schematic view of a system for implementing the present invention. FIG. 2 presents the system as a set of programs running on computer machinery, but those skilled in the art will recognize that the functions described here as software could be implemented in hardware or firmware. Illustrated is a patient 14, to whom a number of electrocardiographic electrodes 16 are affixed. Electrocardiographic electrodes 16 are connected via conducting cables 18 to EKG monitor 20. EKG monitor 20 produces EKG waveform signals which are then fed to EKG front end 21. EKG front end 21 signal conditions and filters the EKG waveform signals and then A/D converts and outputs a stream of discretely sampled EKG waveforms, which for simplicity of understanding will simply be referred to as stream of EKG waveforms 23.

As was done for FIG. 1, the discussion of the system shown in FIG. 2 will relate to one specific heartbeat waveform. It is to be understood that the entire discussion applies equally to every successive waveform within a patient's stream of EKG waveforms 23.

The leading waveform from the stream of EKG waveforms 23 is delivered to microprocessor 25 which is running AMI detection software 27, within which is contained standard AMI detection module 22 and module for detecting AMI when EKG waveform mimics standard AMI detection criteria 29.

The leading waveform from the stream of EKG waveforms 23 is received by standard AMI detection module 22. Standard AMI detection module 22 contains programming sufficient to do the same function as that of method step 42, in that it looks for AMI using standard criteria for AMI detection.

In the event that standard AMI detection module 22 does not detect AMI, the device then passes the electrocardiographic heartbeat waveform to module for detecting AMI when EKG waveform mimics standard AMI detection criteria 29, which delivers the heartbeat waveform to sub-module for determining whether a pre-specified component wave is present within the heartbeat waveforms appearing within each electrocardiographic lead 24. Sub-module for determining whether a pre-specified component wave is present within the heartbeat waveforms appearing within each electrocardiographic lead 24 contains programming sufficient to do the same function as that of method step 50, and looks to see whether or not a certain pre-specified component wave (in the preferred embodiment, this component wave is the S wave) is present.

Sub-module for determining whether a pre-specified component wave is present within the heartbeat waveforms appearing within each electrocardiographic lead 24 passes its determinations to sub-module for calculating wave amplitude ratios for each electrocardiographic lead wherein heartbeat waveform appeared 26. Sub-module for calculating wave amplitude ratios for each electrocardiographic lead wherein heartbeat waveform appeared 26 contains programming sufficient to do the same function as that of method step 52.

Once the wave amplitude ratios have been calculated, the ratios are passed to sub-module for comparing the calculated wave amplitude ratios to pre-specified criteria 28. Sub-module for comparing the calculated wave amplitude ratios to pre-specified criteria contains programming sufficient to compare the calculated wave amplitude ratios to pre-specified criteria, and decide on the basis of this comparison determines whether or not AMI is occurring. In the preferred embodiment this module is programmed to produce the ST/S ratios as were discussed in method step 52, and the compare these calculated ratios with the pre-specified criteria of the classification tree, which is set forth below as FIG. 3. Once the foregoing operations are complete, sub-module for comparing calculated wave amplitude ratios to pre-specified criteria 28 passes the comparison result to sub-module for determining whether AMI is occurring 30.

Sub-module for determining whether AMI is occurring 30 uses the data received from sub-module for comparing each calculated wave amplitude ratio to pre-specified criteria 28 (which usually yields results of AMI or no AMI) in order to determine whether AMI is occurring. If AMI is occurring, sub-module for determining whether AMI is occurring 30 sends that information to device for indicating an occurrence of AMI 32, which indicates the occurrence of an AMI by appropriate means such as a flashing light, a buzzer or any other alarm which may be deemed useful. In the event that sub-module for determining whether an AMI is occurring 30 decides an AMI is not occurring, no signal is sent to device for indicating an occurrence of AMI 32. Once again, as discussed above, the system as just described performs its operation on each successive heartbeat waveform within a patient's stream of EKG waveforms 23.

Figure 3:
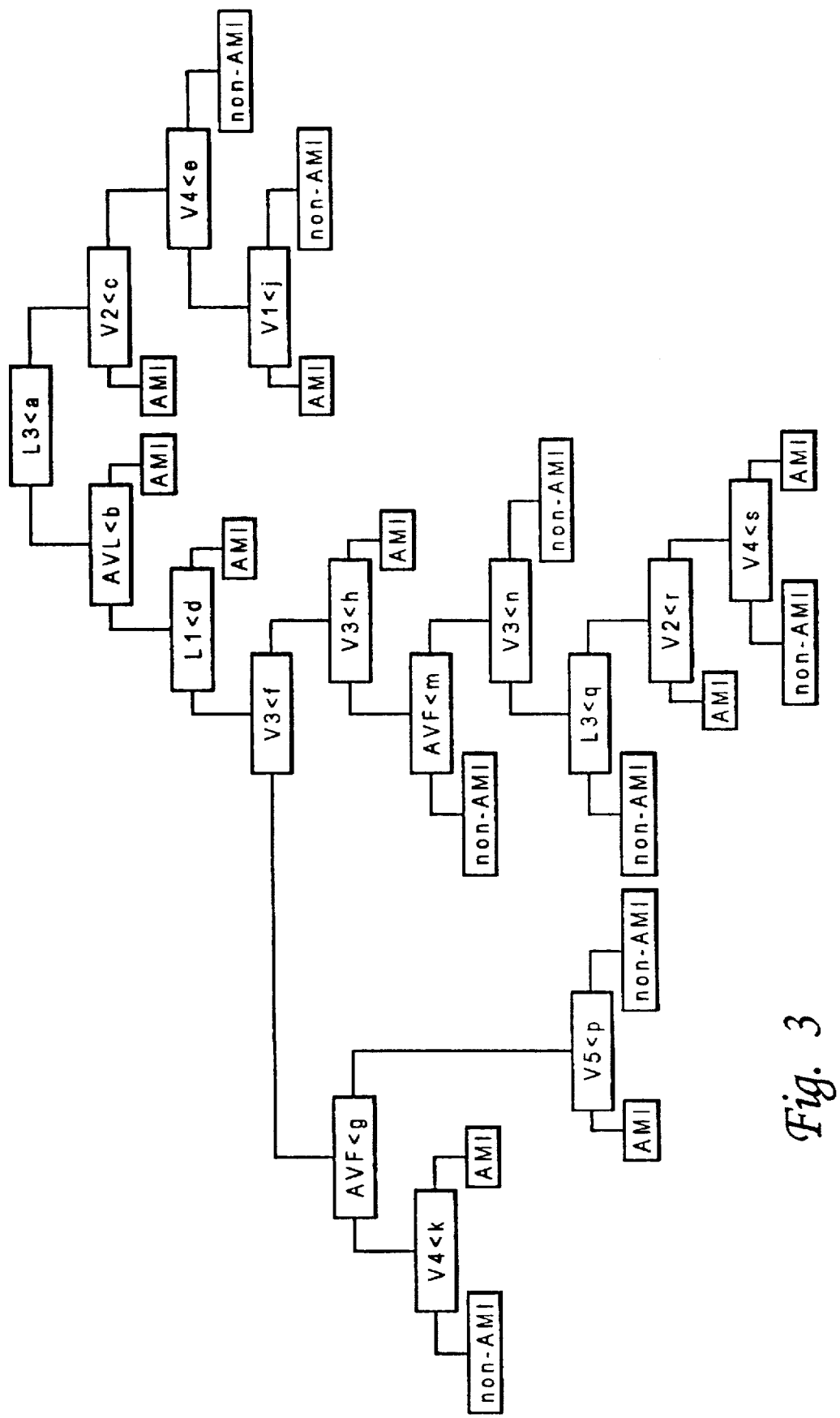
FIG. 3 shows the classification tree used in the preferred embodiment to determine whether or not the calculated ST/S wave amplitude ratios indicate the occurrence of Acute Myocardial Infarction.

With reference now to FIG. 3 which is actually the classification tree used in the preferred embodiment to determine whether the calculated ST/S wave amplitude ratios indicate the occurrence of AMI. Shown is the series of comparisons made within the classification tree, wherein the ST/S wave amplitude ratios for the leads specified within the tree are compared to the values shown. The tree is traversed until a termination point is reached.

It will be recognized by those skilled in the art that the classification tree shown is just one way wherein the criteria indicating the existence of AMI can be pre-specified. The classification tree was obtained by (1) gathering electrocardiographic data for multitudinous numbers of patients; (2) screening this data to find those electrocardiograms which indicated both that AMI was occurring and that the patient had an underlying heart condition which mimicked the criteria normally used to detect AMI; (3) noting the component wave amplitudes within the screened data; and (4) using those noted amplitudes to determine a quantity which would statistically correlate with the heart condition of interest. In the disclosed preferred embodiment, the quantity determined was the ST/S wave amplitude ratio, and the heart condition of interest with which the ST/S wave amplitude ratio correlated was AMI in patients with conditions which mimicked standard AMI detection criteria, but it will be understood by those in the art that the wave amplitude ratios could be used to generate indicators other than the ST/S ratio and statistical correlation matrices other than the classification tree to achieve the functional equivalency to what the inventor has done. It is intended that such functional equivalencies be included within this specification.

Figure 4:
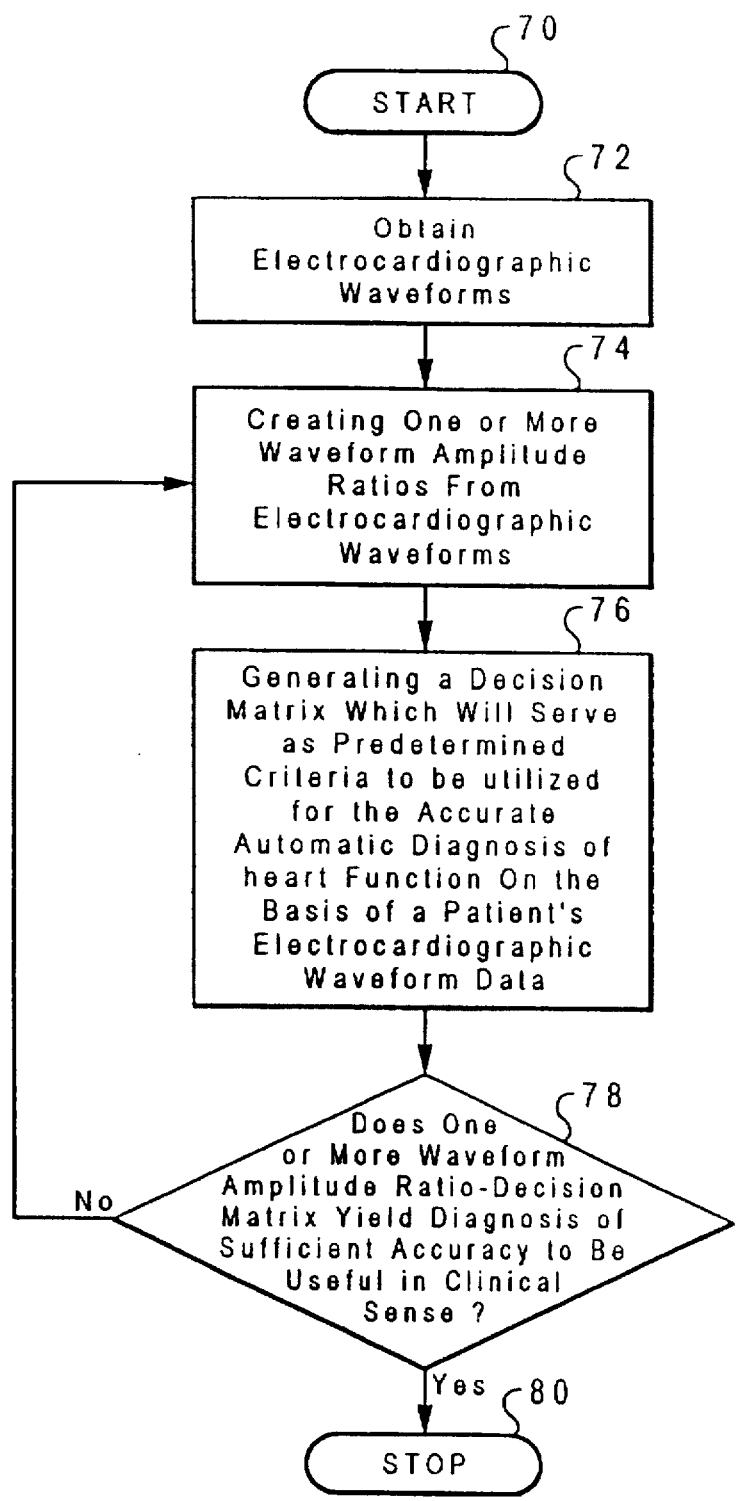
FIG. 4 is a high logical flowchart of the process whereby the predetermined criteria used to diagnosis a patient's heart function is generated.

With reference now to FIG. 4 there is depicted a high-level logical flowchart of the process whereby the predetermined criteria used to diagnosis a patient's heart function is generated. That is, FIG. 4 illustrates the method and process by which the classification tree of FIG. 3 was created.

Method step 70 shows the start of the process. Method step 72 depicts the obtainment of electrocardiographic waveforms indicative of heart conditions of interest. In practice, these waveforms can be obtained by consulting learned treatises in electrocardiography, downloading such waveforms from the Internet, or consulting qualified electrocardiologists on the question of what electrocardiographic waveforms indicate certain heart conditions of interest. Some or all of the waveforms so obtained can then be collected together.

Method step 74 illustrates the creation of one or more wave amplitude ratios from the collected electrocardiographic waveforms. With respect to the preferred embodiment disclosed above, this method step illustrates how the ST/S wave amplitude ratio was obtained. The creation of one or more wave amplitude ratios from the collected electrocardiographic waveforms is an empirical process by which those skilled in the art deem certain of the wave amplitude components of the electrocardiographic waveform, or certain ratios of the wave amplitude components of the electrocardiographic data, to be indicative of the heart conditions of interest. It is to be understood that a wave amplitude component can be termed a ratio in that it can be that component divided by one.

Method step 76 shows the generation of a decision matrix which will serve as predetermined criteria to be utilized for the accurate automatic diagnosis of heart function on the basis of a patient's electrocardiographic waveform data. This decision matrix is generated by taking the one or more wave amplitude ratios created in method step 74 and statistically correlating it with the electrocardiographic waveforms indicative of certain heart conditions of interest with which were obtained in method step 72. The statistical correlation can be done with any number of commercial statistical packages. Once the statistical decision tree has been generated, it is subjected to a number of tests whereby the accuracy of using the one or more wave amplitude ratios which were created in method step 74 in conjunction with the decision matrix generated in method step 76 is accessed.

Method step 78 shows a decision point. In this decision point it is determined whether the one or more wave amplitude ratios created in method step 74 used in conjunction with the generated decision matrices generated in method step 76 yields accurate enough results to be useful in a clinical sense. If the answer is yes, then one proceeds to method step 80 which is the end of the process. Otherwise, one proceeds back to method step 74 wherein another one or more wave amplitude ratios is created and again used to generate another statistical decision matrix in method step 76. The loop comprised of method steps 74, 76 and 78 continues until the process yields at least one wave amplitude ratio-decision matrix combination which will generate diagnosis of sufficient accuracy to be useful in a clinical sense, as is depicted in method step 78. Once this criterion has been satisfied one proceeds to method step 80 and the process stops.

Figure 5:
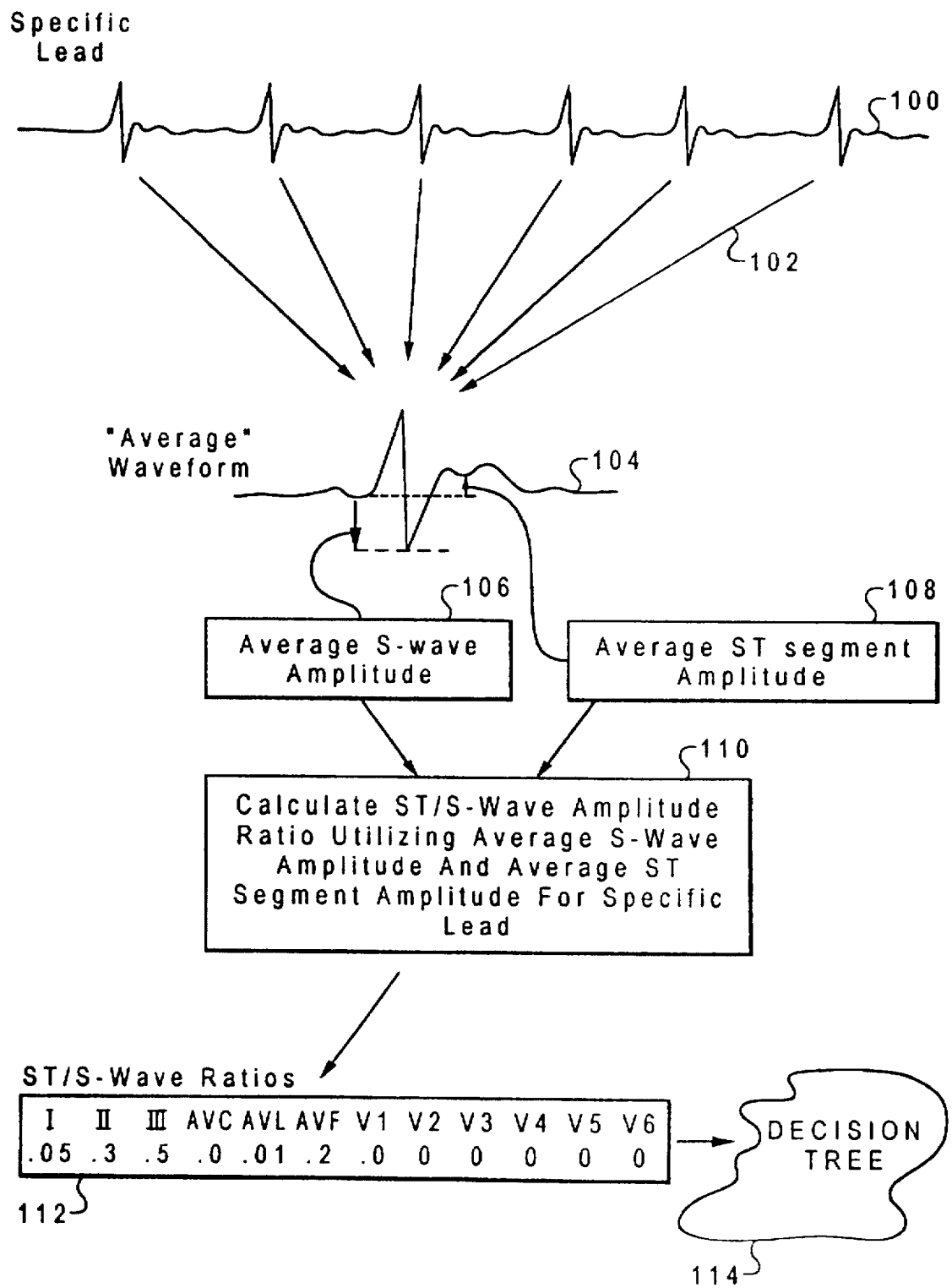
FIG. 5 is a partially schematic illustration of the way in which 10 or 11 seconds of electrocardiographic waveform data is used to construct an average ST/S wave amplitude ratio as is discussed in method step 52 of FIG. 1.

Refer now to FIG. 5, which shows a partially schematic illustration of the way in which 10 or 11 seconds of data is used to construct an average ST/S wave amplitude ratio as was discussed in method step 52 of FIG. 1. Shown is 10 or 11 second wavetrain of electrocardiographic waveforms 100 which appears within one of the electrocardiographic leads (e.g., aVF). Arrows representing averaging 102 depict the generation of an average "waveform" 104 which is drawn upon the entire 10 or 11 second wavetrain of electrocardiographic waveforms 100. In actuality, what is actually calculated is an average S wave component amplitude 106 and an average ST segment amplitude 108 as discussed previously, but for clarity of understanding a conceptual average "waveform" 104 has been illustrated. Next, it is shown that an ST/S wave amplitude ratio is calculated using the average S wave amplitude 106 and average ST segment amplitude 108, which is denoted as single ST/S wave amplitude ratio per lead 110. As has been discussed, there is at least one ST/S wave amplitude ratio calculated for each lead. This fact is illustrated in table of example ST/S wave ratios 112. These calculated values are then passed to decision tree 114, which is similar to the predetermined criteria as in method step 54, and which in the preferred embodiment equates to the classification tree of FIG. 3.

While an illustrative embodiment has been particularly shown and described, it will be understood by those skilled in the art that various changes in form and detail may be made therein without departing from the spirit and scope of the illustrative embodiment.

What is claimed is:

1. A method for detecting an occurrence of Acute Myocardial Infarction on the basis of a patient's electrocardiographic waveform data, said electrocardiographic waveform data including at least one heartbeat waveform and wherein said at least one heartbeat waveform comprises at least one of P, Q, R, S, and T component waves and wherein said at least one heartbeat waveform can be partitioned to form an ST segment, even when said patient has an underlying heart condition which mimics standard criteria for detecting Acute Myocardial Infarction, said method comprising the steps of:

obtaining one or more electrocardiographic leads having said patient's electrocardiographic waveform data;

determining whether or not at least one predetermined component wave is present within each successive heartbeat waveform appearing within each electrocardiographic lead;

in response to said determining step, calculating at least one wave amplitude ratio, wherein said wave amplitude ratio is a ratio of an ST segment to said at least one predetermined component wave, for each electrocardiographic lead in which said each successive heartbeat waveform appears; and in response to said calculated at least one wave amplitude ratio for each electrocardiographic lead in which said each successive heartbeat waveform appears meeting predetermined criteria, indicating an occurrence of Acute Myocardial Infarction.

2. The method of claim 1, wherein said calculating step of determining whether or not at least one predetermined component wave is present within each successive heartbeat waveform appearing within each electrocardiographic lead comprises the step of determining whether or not an S wave is present within each successive heartbeat waveform appearing within each electrocardiographic lead.

3. The method of claim 2, wherein said calculating step further comprises the steps of:

for said each electrocardiographic lead in which said each successive heartbeat waveform appears and in which it is determined that no S wave is present, assigning an ST/S wave amplitude ratio to be zero; and for said each electrocardiographic lead in which said each successive heartbeat waveform appears and in which it is determined that an S wave is present:

obtaining an ST segment amplitude;

obtaining an S wave amplitude; and calculating said ST/S wave amplitude ratio by dividing an ST amplitude by an amplitude of said S wave.

4. The method of claim 1, wherein said step of indicating an occurrence of Acute Myocardial Infarction comprises the steps of:

traversing a classification tree utilizing said calculated at least one wave amplitude ratio for each electrocardiographic lead in which said each successive heartbeat waveform appears;

in response to said traversing step, classifying said calculated at least one wave amplitude ratio for each electrocardiographic lead in which said each successive heartbeat waveform appears as either indicative of or not indicative of Acute Myocardial Infarction; and in response to said classifying step, indicating the occurrence of Acute Myocardial Infarction if said calculated at least one wave amplitude ratio for each electrocardiographic lead in which said each successive heartbeat waveform appears was classified as indicative of Acute Myocardial Infarction.

5. A system for detecting an occurrence of Acute Myocardial Infarction on the basis of a patient's electrocardiographic waveform data, sad electrocardiographic waveform data including at least one heartbeat waveform and wherein said at least one heartbeat waveform comprises at least one of P, Q, R, S, and T component waves and wherein said at least one heartbeat waveform can be partitioned to form an ST segment, even when said patient has an underlying heart condition which mimics standard criteria for detecting Acute Myocardial Infarction, said system comprising:

means for obtaining one or more electrocardiographic leads having said patient's electrocardiographic waveform data;

means for determining whether or not at least one predetermined component wave is present within each successive heartbeat waveform appearing within each electrocardiographic lead;

means, responsive to said determining step, for calculating at least one wave amplitude ratio, wherein said wave amplitude ratio is a ratio of an ST segment and said at least one predetermined component wave, for each electrocardiographic lead in which said each successive heartbeat waveform appears; and means, responsive to said calculated at least one wave amplitude ratio for each electrocardiographic lead in which said each successive heartbeat waveform appears meeting predetermined criteria, for indicating an occurrence of Acute Myocardial Infarction.

6. The system of claim 5, wherein said means for determining whether or not at least one predetermined component wave is present within each successive heartbeat waveform appearing within each electrocardiographic lead comprises means for determining whether or not an S wave is present within each successive heartbeat waveform appearing within each electrocardiographic lead.

7. The system of claim 6, wherein means for calculating further comprises:

for said each electrocardiographic lead in which said each successive heartbeat waveform appears and in which it is determined that no S wave is present, means for assigning an ST/S wave amplitude ratio to be zero; and for said each electrocardiographic lead in which said each successive heartbeat waveform appears and in which it is determined that an S wave is present:
means for obtaining an ST segment amplitude;
means for obtaining an S wave amplitude; and
means for calculating said ST/S wave amplitude ratio by dividing an ST amplitude by an amplitude of said S wave.

8. The system of claim 5, wherein said means for indicating an occurrence of Acute Myocardial Infarction comprises:

means for traversing a classification tree utilizing said calculated at least one wave amplitude ratio for each electrocardiographic lead in which said each successive heartbeat waveform appears;

means, responsive to said traversing step, for classifying said calculated at least one wave amplitude ratio for each electrocardiographic lead in which said each successive heartbeat waveform appears as either indicative of or not indicative of Acute Myocardial Infarction; and means, responsive to said classifying step, for indicating the occurrence of Acute Myocardial Infarction if said calculated at least one wave amplitude ratio for each electrocardiographic lead in which said each successive heartbeat waveform appears was classified as indicative of Acute Myocardial Infarction.

* * * * *